(12) United States Patent
Detmar et al.

(10) Patent No.: US 11,896,707 B2
(45) Date of Patent: Feb. 13, 2024

(54) COSMETIC PREPARATIONS COMPRISING DAPHNE EXTRACTS

(71) Applicants: ETH Zurich, Zürich (CH); Universität Basel, Basel (CH)

(72) Inventors: Michael Detmar, Boppelsen (CH); Epameinondas Gousopoulos, Zürich (CH); Olivier Potterat, Aesch (CH); Jihye Kim, Zürich (CH); Adriana Sliwa-Primorac, Vienna (AT); Antonia Elisabeth Schantl, Zürich (CH); Maria Teresa Faleschini, Pratteln (CH); Matthias Hamburger, Arlesheim (CH)

(73) Assignees: ETH Zurich, Zurich (CH); Universität Basel, Basel (CH)

( * ) Notice: Subject to any disclaimer, the term of this patent is extended or adjusted under 35 U.S.C. 154(b) by 246 days.

(21) Appl. No.: 17/312,538

(22) PCT Filed: Dec. 10, 2019

(86) PCT No.: PCT/EP2019/084376
§ 371 (c)(1),
(2) Date: Jun. 10, 2021

(87) PCT Pub. No.: WO2020/120451
PCT Pub. Date: Jun. 18, 2020

(65) Prior Publication Data
US 2022/0054396 A1    Feb. 24, 2022

(30) Foreign Application Priority Data
Dec. 10, 2018 (EP) .................... 18211306

(51) Int. Cl.
*A61K 36/00* (2006.01)
*A61K 8/9789* (2017.01)
*A61K 8/49* (2006.01)
*A61Q 19/08* (2006.01)

(52) U.S. Cl.
CPC .......... *A61K 8/9789* (2017.08); *A61K 8/4973* (2013.01); *A61Q 19/08* (2013.01)

(58) Field of Classification Search
CPC ..................................................... A61Q 19/08
See application file for complete search history.

(56) References Cited

U.S. PATENT DOCUMENTS

| | | |
|---|---|---|
| 2007/0299018 A1 | 12/2007 | Prost et al. |
| 2009/0170930 A1* | 7/2009 | He ................. A61P 25/00 |
| | | 514/457 |
| 2016/0367499 A1 | 12/2016 | Detmar et al. |

FOREIGN PATENT DOCUMENTS

| CN | 1883618 B * | 9/2011 |
|---|---|---|
| CN | 106890365 A | 6/2017 |
| EP | 2711014 A2 | 3/2014 |
| KR | 20150121492 A | 10/2015 |
| WO | 2015079469 A1 | 6/2015 |
| WO | 2017146341 A1 | 8/2017 |
| WO | 2019032979 A1 | 2/2019 |

OTHER PUBLICATIONS

Liao et al, New phenolic components from Daphne giraldii. Helvetica Chimica Acta (2005), vol. 88, No. 11, pp. 2873-2878 (Year: 2005).*
Hickey, T.A et al. "Irritant Contact Dermatitis in Humans from Phorbol and Related Esters" Toxicon, Jan. 1, 1981, pp. 841-850, vol. 19, No. 6.
Jin, Y. et al. "A Review on Daphnane-Type Diterpenoids and Their Bioactive Studies", Molecules, 2019, pp. 1-14, vol. 24, No. 9.
Mintel, Eye Rescue Cream, 2016, retrieved from www.gnpd.com.
Schulz, M.M et al., "Phenotype-based high content chemical library screening identifies statins as inhibitors of in vivo lymphangiogenesis" PNAS, 2012, pp. 1-10.

* cited by examiner

*Primary Examiner* — Qiuwen Mi
(74) *Attorney, Agent, or Firm* — Larson & Anderson, LLC (57) ABSTRACT

The present invention relates to the use of plant extracts from the genus *Daphne* for the cosmetic treatment of the skin and to cosmetic preparations which comprise extracts of *Daphne giraldii* and/or *Daphne gnidium* or other members of the genus *Daphne* containing daphnetoxin and/or other daphnane diterpenoids for skin treatment. The plant extracts and cosmetic preparations are particularly useful for stimulation of the lymphatic system.

18 Claims, 7 Drawing Sheets

COSMETIC PREPARATIONS COMPRISING DAPHNE EXTRACTS

The present invention relates to the use of plant extracts from the genus *Daphne* for the cosmetic treatment of the skin and to cosmetic preparations, which comprise extracts of *Daphne giraldii* and/or *Daphne gnidium* and/or other members of the genus *Daphne* containing daphnetoxin and/or other daphnane diterpenoids for skin treatment. The plant extracts and cosmetic preparations are particularly useful for stimulation of the lymphatic system.

Anti-aging cosmetic preparations with variable effects are widely known. Also cosmetic preparations comprising plant extracts which are aimed at skin treatment are known per se and well investigated. In the past, there have already been various compositions in cosmetics and in dermatology whose task was to protect skin, in particular human skin. Nevertheless, there continues to be the need to improve or to modify skin protection because the environmental conditions and also living conditions and habits of users are changing.

Pharmaceutical and cosmetical applications of *Daphne* extracts are known in the field.

US2007/0299018 describes purified derivatives of genkwanin, obtainable from plants of the genus *Prunus, Gnidia* or *Daphne*. The document further relates to the cosmetic and dermatological use of such derivatives for improving the texture of the skin.

WO2017/146341 describes cosmetic compositions for treating wounds, alleviating skin wrinkles, and preventing skin aging. The compositions comprise purified compounds, specifically daphnin (a coumarin) and isoquercitrin (a flavonoid).

KR20150121492 describes cosmetic compositions with anti-wrinkle properties. The compositions comprise purified compounds, specifically daphnetin which belongs to the group of coumarins.

The commercial product mintel Eye Rescue Cream comprises a non-characterized *Daphne odora* callus extract. According to the manufacturer, it helps reducing the appearance of eye bags and cark circles.

CN106890365 describes therapeutic compositions comprising *Daphne* extracts. The document is silent on cosmetic applications. The document is silent on daphnane diterpenoids.

WO2015/079469 describes *Daphne laureola* extracts in the treatment of dermatopathies; particularly psoriasis. The document is silent on daphnane diterpenoids.

EP2711014 describes *Daphne genkwa* extracts in the treatment of atopic dermatitis. Specifically mentioned in that document are genekwadaphnin and yuanhuacine, both compounds inducing the secretion of type I cytokine and thereby treat atopic dermatitis.

US20160367499 discloses cosmetic and pharmaceutical compositions comprising lipophilic extracts of members of the Iridaceae family. According to this document, the lymphatic system is stimulated by such extracts, making it useful in the treatment of diseases related to impaired lymphatic function, including skin inflammation. The document is silent on *Daphne* extracts.

WO2019/032979, published after filing, discloses topical compositions comprising ximenytic acid. The document speculates about adding further components to the topical compositions, such as *Daphne gnidium* flower extract.

Given the above, the prior art failed to identify the beneficial effects of diterpenoids extracted from plants of the genus *Daphne*, particularly its cosmetic uses due to the stimulation of the lymphatic system.

In consequence, there is a need for new applications of *Daphne* extracts and/or for improved cosmetic treatment of the skin.

Thus, it is an object of the present invention to mitigate at least some of these drawbacks of the state of the art. In particular, it is an aim of the present invention to provide new uses of *Daphne* extracts and new preparations adapted to such uses.

These objectives are achieved by the use as defined in claim 1 and the preparations as defined in claim 8. Further aspects of the invention are disclosed in the specification and independent claims, preferred embodiments are disclosed in the specification and the dependent claims.

The present invention will be described in more detail below. It is understood that the various embodiments, preferences and ranges as provided/disclosed in this specification may be combined at will. Further, depending of the specific embodiment, selected definitions, embodiments or ranges may not apply.

Unless otherwise stated, the following definitions shall apply in this specification:

As used herein, the term "a", "an", "the" and similar terms used in the context of the present invention (especially in the context of the claims) are to be construed to cover both the singular and plural unless otherwise indicated herein or clearly contradicted by the context.

As used herein, the terms "including", "containing" and "comprising" are used herein in their open, non-limiting sense. The term "containing" shall include "comprising", "essentially consisting of" and "consisting of".

The term "treatment" shall include the prevention, inhibition and delay of progression of negative effects and/or the promotion of desirable effects.

The present invention will be better understood by reference to the figures;

FIG. 7 shows results of LEC sprouting tests and LEC proliferation test as outlined in example 7.

A: x-axis from left to right: 0.1% DMSO VEGF-A—Daphnetoxin nanomolar; y-axis: sprouts/bead.

B: x-axis from left to right: 0.1% DMSO—Daphnetoxin nanomolar; y-axis: % control.

In more general terms, in a first aspect, the invention relates to the use of plant extracts from the genus *Daphne*, particularly daphnane diterpenoids, for the cosmetic treatment of the skin. It was surprisingly found that such extracts stimulate the lymphatic system and thus provide for a number of beneficial cosmetic applications. This aspect of the invention shall be explained in further detail below:

Plants from the genus *Daphne*: This genus is well-known and includes between 70 and 95 species of deciduous and evergreen shrubs in the family Thymelaeaceae, native to Asia, Europe and north Africa. In an embodiment of the invention, plants from the genus *Daphne* are selected from *Daphne giraldii* and *Daphne gnidium*. In an embodiment of the invention, plants from the genus *Daphne* exclude *Daphne genkwa*.

Plant extracts: Preparing plant extracts is well-known in the field. Known technologies may be applied to obtain plant extracts from plants of the genus *Daphne*.

Plant extracts from the genus *Daphne* contain characteristic diterpenoids ("daphnane diterpenoids"). The term daphnane diterpenoids shall include compounds comprising the following 5/7/6 tricyclic carbon skeleton of formula (I):

(I)

In formula (I), only carbon-atoms and their numbering are shown. Neither the stereochemistry, potential multiple bonds nor hetero atoms or substituents are included in formula (I).

In an embodiment of the invention, daphnane diterpenoids comprise, particularly consist of, daphnetoxin.

Daphnetoxin is shown in formula (I-1), (I-1)

Daphnetoxin has a pronounced effect on stimulating the lymphatic system.

In an embodiment of the invention, the term daphnane diterpenoids excludes genekwadaphnin and yuanhuacine; these diterpenoids induce secretion of type I cytokines.

Plant extracts are obtainable by using a polar solvent or mixture of polar solvents. Suitable polar solvents include: C1-C4 alcohols (including methanol, ethanol, propanol, and butanol), C1-C4 diols ("glycols"; including ethylene-, propylene-, butylene-glycol), glycerol, acetone, ethyl acetate). Such polar solvents may be combined with water. Further, plant extracts are obtainable by using an apolar solvent. Suitable apolar solvents include: C4-C10 alkanes (including (cyclo)-hexane), C1-C2 alkylhalogenides (including methylene chloride, chloroform), C1-C4 dialkylethers (including diethylether, t-butyl-methylether). Still further, plant extracts may be obtained by using supercritical fluids (particularly $CO_2$); and/or mixtures of $CO_2$ with C1-C3 alcohols (particularly: methanol, ethanol, propanol) or with acetone.

Fresh or dried extracts from the plant's root, particularly bark root, may be used. Further, fresh or dried extracts from the plant's green part may be used. When using the green part, extracts may origin from the green part as a whole or from one or more of flowers, fruits, leaves, stems and stalks.

The term "plant extracts" shall include (i) crude extracts obtained from the plant or parts thereof and (ii) extracts enriched in daphnane diterpenoids, obtained from the plant or parts thereof, and (iii) purified substances therefrom.

Stimulation of the lymphatic system: Lymph vessels fulfill an important role in order to maintain the microenvironment surrounding tissue in a constant state by removing unwanted substances present in skin as well as water and protein constantly escaping from blood vessels. It was found that plant extracts as described herein activate the lymphatic system, particularly the lymphatic vasculature. This action was tested using in vitro test methods. In particular, using a model of sprouting assay developed previously (c.f. ADD Reference SCHULZ MM ET AL., PNAS 2012: PMID 22949700), a library of plant extracts was screened for extracts inducing lymphatic endothelial cell (LEC) sprouting. The key findings were further verified and analysed to characterize the active ingredients. The advantageous effects of the plant extracts were further confirmed by conducting relevant cell proliferation assays, in vitro migration assays and LEC tube formation assays. Given the positive results in all above mentioned assays, one can deduct the positive effect of the plant extracts and the active ingredient thereof, on improving lymphatic vascular function.

The invention thus relates to the use of plant extracts from the genus *Daphne* for promoting activation of the lymphatic system, particularly for stimulating the lymphatic vasculature.

The above findings are further and subsequently linked to skin detoxification and anti-aging properties, as key contributions of the improved function of the lymphatic vasculature. Accordingly, the cosmetic treatment provides for a number of desirable effects. In an advantageous embodiment, the cosmetic treatment provides for rejuvenation of the skin. In a further advantageous embodiment, the cosmetic treatment provides for an anti-aging effect of the skin. In a further advantageous embodiment, the cosmetic treatment includes puffy-eye treatment. In a further advantageous embodiment, the cosmetic treatment provides for detoxification of the skin. In a further advantageous embodiment, the cosmetic treatment increases firmness of the skin. In a further advantageous embodiment, the cosmetic treatment provides for an anti-swelling effect.

The plant extracts described herein may be used in a broad concentration range to achieve the desirable effects described. A suitable range may be determined by routine experiments, considering the type of cosmetic composition and the effect desired. Useful concentration ranges depend on the type of plant extract to be used. When using crude extracts obtained from the plant or parts thereof, suitable concentration are in the range of 0.0001-50 wt %, such as the range of 0.0001-10 wt %. When using extracts enriched in daphnane diterpenoids, obtained from the plant or parts thereof, suitable concentration are in the range of 0.00001-20 wt %, such as the range of 0.00001-5 wt %. When using purified substances therefrom, such as daphnetoxin, suitable concentration are in the range of 10 pM-100 mM, such as the range of 10 pM-10 nM.

Accordingly, the concentration of daphnane diterpenoids may vary over a broad range, typically 0.00001-1 wt %. Suitable concentrations, as discussed herein, may be determined by the skilled person, depending on the intended use, formulation and type of extract.

In a second aspect, the invention relates to cosmetic preparations comprising plant extracts of *Daphne giraldii* and/or *Daphne gnidum* as well as other members of the *Daphne* genus. This aspect of the invention shall be explained in further detail below:

As discussed above, such plant extracts of *Daphne* contain daphnane diterpenoids.

In one embodiment, the daphnane diterpenoids comprise or consist of daphnetoxin. It was found that daphnetoxin is particularly effective in stimulating the lymphatic system.

In one embodiment, the daphnane diterpenoids are essentially free of, or free of, genekwadaphnin and yuanhuacine. It was found that these compounds are useful in inducing secretion of type I cytokines but less useful in stimulating the lymphatic system. Accordingly, the amount of genekwadaphnin and yuanhuacine may be very low, typically below $1/50$ wt/wt, when compared to the total amount of daphnane diterpenoids.

As discussed above, these plant extracts were found particularly useful in cosmetic compositions for skin treatment. Suitably, the concentration of daphnane diterpenoids in such cosmetic compositions is in the range 0.00001-1 wt %.

Cosmetic preparation: Cosmetic preparations are known per se. However, until now no such preparation comprising plant extracts from members of the genus *Daphne*, particularly from *Daphne giraldii* and/or from *Daphne gnidium* were described. The invention therefore provides for such cosmetic preparations. Accordingly, such preparations comprise plant extracts containing daphnane diterpenoids, particularly daphnetoxin.

The skilled person is in a position to formulate cosmetic preparations containing such extracts. Suitable amounts of plant extract within the cosmetic preparation may vary over a broad range and depend (inter alia) on the type of plant extract used in the cosmetic preparation. Suitable are, for example, 0.0001-50 wt % in case of crude plant extracts; 0.00001-20 wt % in case of enriched extracts; 10 pM-100 mM in case of purified substances of said plant extracts within said cosmetic preparation. The indicated range is broad, due to the large variety of plant extracts suitable and due to the large spectrum of possible preparations. Suitable plant extracts may be obtained as discussed above, first aspect of the invention.

Formulations: Cosmetic preparations may be provided in any conventional form known to the skilled person. In one embodiment, the cosmetic preparation is in the form of a liquid formulation. Such liquid formulations include gels, lotions, milks, emulsions, a spray, an oil and foams. In one further embodiment, the cosmetic preparation is in the form as a semisolid formulation or as a solid formulation. Such formulations include creams, ointments, powders and sticks. These types of formulations are known per se.

In a further aspect, the invention provides for a skin detoxification ameliorant comprising plant extracts from the genus *Daphne* and for a skin anti-aging ameliorant comprising plant extracts from the genus *Daphne*.

Excipients: Cosmetic preparations typically comprise excipients. Such excipients are known per se and the skilled person is in a position to select them in view of the intended form of application for the plant extracts described herein. Accordingly, the invention provides for a cosmetic preparation comprising plant extracts as described herein and further comprising one or more cosmetic excipients; said excipients preferably being selected from the group consisting of emollients, moisturizers, thickeners, emulsifiers, colorings, detergents, disinfectants, antioxidants, buffers, matting agents, exfoliating agents, aromas, essential oils, vitamins, and UV filters.

Extracellular matrix components: It was further found that extracellular matrix compounds beneficially improve or support the cosmetic effects obtained when using extracts from the genus *Daphne*. Particularly, a positive synergistic effect is observed when providing cosmetic compositions as described herein further containing extracellular matrix compounds. Such extracellular matrix components are known to the skilled person and include collagen, elastin, and hyaluronic acid; particularly hyaluronic acid.

Accordingly, the invention also provides for the use of plant extracts from the genus *Daphne* in combination with extracellular matrix components for the cosmetic treatment of the skin. Further, the invention provides for cosmetic preparations for skin treatment comprising plant extracts from members of the genus *Daphne* and extracellular matrix components both as described herein.

In a third aspect, the invention relates to a method of cosmetically treating the skin. This method comprises the step of applying to skin in need thereof a preparation as described herein, second aspect of the invention. This aspect shall be described in further detail below:

Cosmetic treatment: It is to be understood that cosmetic treatment excludes therapeutic treatments and therefore does not require supervision by a physician.

Advantageously, the skin is treated to stimulate the lymphatic system.

The aforementioned extracts of *Daphne* are extremely useful for supporting the function of lymph vessels. Symptoms accompanying lymph vessel dysfunction are discussed herein. The extracts of *Daphne* are effective for treating the lymph vessels, particularly for stimulating the lymphatic vasculature.

As discussed above, the stimulation of the lymphatic system provides for a number of desirable effects. Accordingly, the invention provides for a method of cosmetically treating the skin to effect one or more of the following: rejuvenation of the skin; anti-aging of the skin; puffy-eye treatment; detoxification of the skin; firmness of the skin and anti-swelling effect.

Still further, the inventive treatment protects the skin. Still further, the inventive treatment counteracts swelling of the skin. Still further, the inventive treatment increases the longevity of skin cells. Still further, the inventive treatment counteracts intrinsic and/or extrinsic skin ageing.

As a consequence, the invention provides for a cosmetic method for treating the skin, said method comprises the step of applying a composition as described herein to the skin of a subject requiring activation of lymph vessel function. Said treatment particularly includes the cosmetic treatments discussed above.

To further illustrate the invention, the following examples are provided. These examples are provided with no intent to limit the scope of the invention.

Ex. 1: Library Screening of 1954 Plant Extracts

Figure 1:
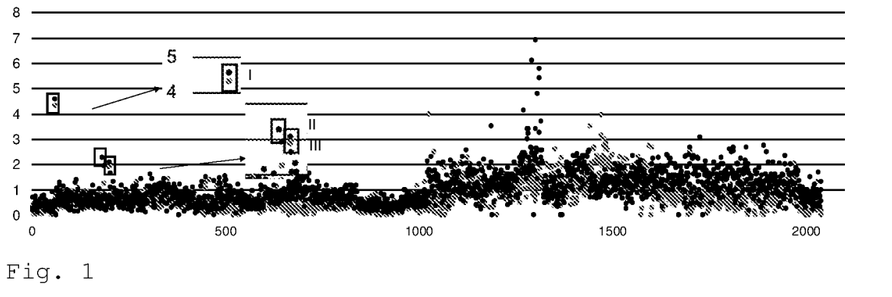
FIG. 1 shows results of a library screening of 1954 plant extracts as outlined in example 1. x-axis: # of plant extracts; y-axis: sprouts/bead.

After a 24 hour incubation of fluorescently labeled LEC (lymphatic endothelial cell)-covered dextran beads with 10 pg/mL of extracts from a library of 1954 plant-derived samples, sprout formation was assessed by determining the ratio of sprouts per bead. 0.1% DMSO served as a vehicle control. Each extract was tested as 1-plicate and the entire library was screened in two independent replicates. FIG. 1 shows the results obtained for replicate 1 and 2; enlarged are:

D. gnidium $CH_2Cl_2$: 4.3 and 4.6 sprouts/bead
D. giraldii MeOH: 2.3 and 2.4 sprouts/bead
D. giraldii $CH_2Cl_2$: 2.0 and 1.7 sprouts/bead
D. giraldii EtOAc: 1.9 and 2.1 sprouts/bead The results indicate that various species and various extracts of *Daphne* are suitable for the uses and applications described herein.

Ex. 2: Extraction Experiments

A: Plant Extracts from the Genus *Daphne*

Powdered dried leaves of *Daphne gnidium* (collected in 2006 in Italy) (171 g) were percolated with $CH_2Cl_2$ (1.1 L) to provide after evaporation to dryness under reduced pressure 12.4 g of leaf extract.

Powdered root bark of *Daphne giraldii* (purchased in 2008 in an herbal market in China) (475 g) were percolated with $CH_2Cl_2$ (4 L) to provide after evaporation to dryness under reduced pressure 13.3 g of root bark extract.

Such extracts are useful for manufacturing a cosmetic preparation as described herein.

B: Isolation of Daphnetoxin

Powdered dried stems of *Daphne gnidium* (collected in 2006 in Italy) (57 g) were percolated with $CH_2Cl_2$ (1.1 L) to provide after evaporation to dryness under reduced pressure 911 mg of stem extract.

The extract was separated by repeated injections on a semi-preparative RP-18 HPLC column (60-100% MeOH in 30 min) to yield pure daphnetoxin (10.4 mg).

Ex. 3: LEC Sprouting of *D. gnidium* and *D. giraldii* Extracts

Figure 2:
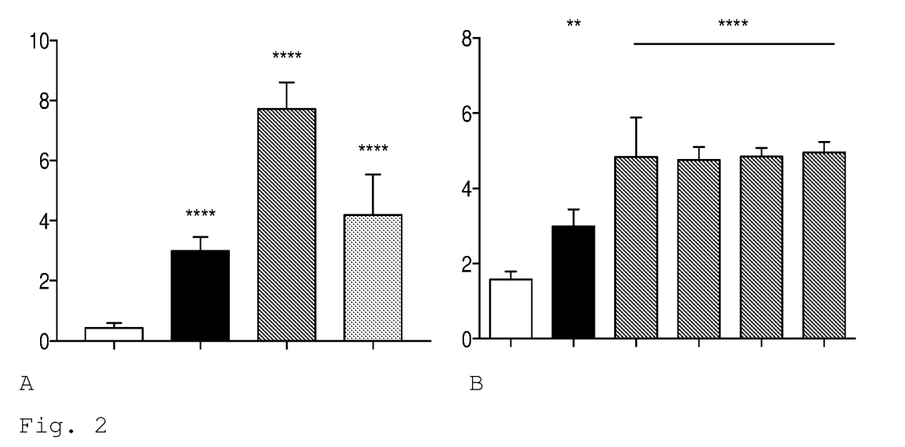
FIG. 2 shows results of LEC sprouting experiments as outlined in example 2 and 5 respectively.
A: x-axis from left to right: 0.1% DMSO—VEGF-A—*D. gnidium*—*D. giraldii*; y-axis: sprouts/bead.
B: x-axis from left to right: 0.1% DMSO Daphnetoxin 0.3/1.0/3.0/10 micromolar; y-axis: sprouts/bead.

The *Daphne gnidium* (*D. gnidium*) and *Daphne giraldii* (*D. giraldii*) extracts as obtained from example 2 induced LEC sprouting at 10 μg/mL. Sprout formation was assessed by determining the ratio of sprouts per bead. 0.1% DMSO and VEGF-A (20 ng/mL) served as negative and positive controls respectively. Each sample was tested as 6-replicates, results are shown in FIG. 2A.

The results indicate that *D. gnidium* and *D. giraldii* extracts activate the lymphatic endothelium.

Figure 3:
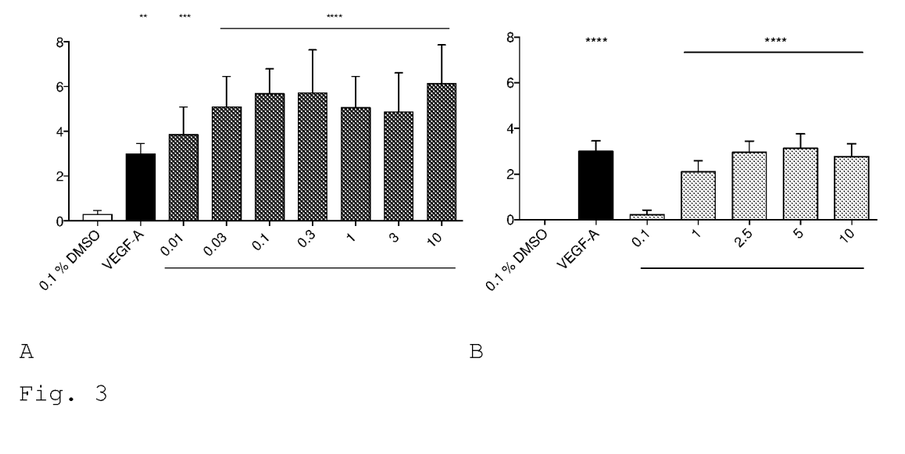
FIG. 3 shows dose response of *D. gnidium* (FIG. 3A) and *D. giraldii* (FIG. 3B) in spouting assay. x-axis from left to right: 0.1% DMSO—VEGF-A—*Daphne* extract (concentration microgram/mL); y-axis: sprouts/bead.

*D. gnidium* extract ($CH_2Cl_2$) (A) and *D. giraldii* ($CH_3OH$) extracts (B) significantly induced LEC sprouting at various concentrations.

0.1% DMSO served as a vehicle control and VEGF-A (20 ng/mL) as a positive control. Results are reported in FIGS. 3A and 3B.

The results indicate for both extracts a trend towards increased activity with higher concentrations (dose-dependent manner), which seemed to reach a plateau.

Ex. 4: Selectivity of *D. gnidium* Extracts

Figure 4:
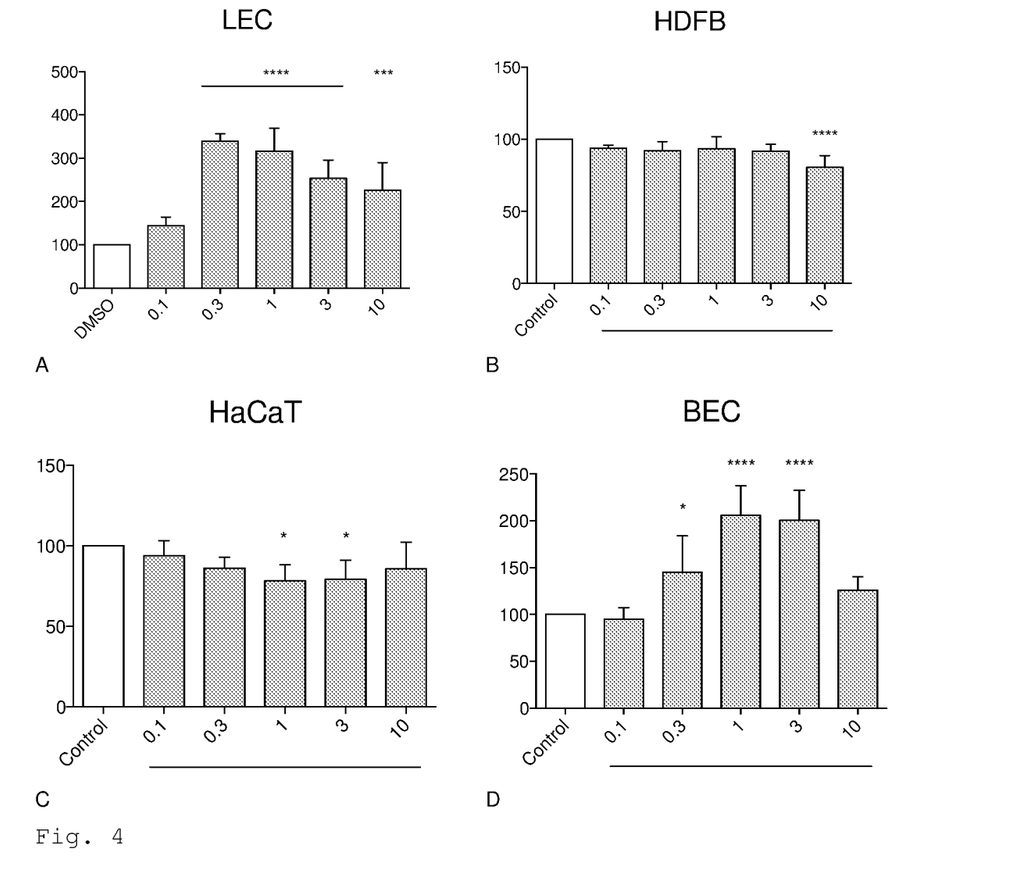
FIG. 4 shows results of endothelial cell proliferation in vitro as outlined in example 4. x-axis from left to right: 0.1% DMSO—*Daphne* extract (concentration microgram/mL); y-axis: % of control. A: LEC; B: HDFB; C: HaCaT; D: BEC.

Selectivity was examined using *D. giraldii* extracts. *D. giraldii* extract ($CH_3OH$) promoted endothelial cell proliferation in vitro. *D. giraldii* extracts induced significantly LEC (A) and BEC (D) proliferation at concentrations ranging between 0.3 to 10 μg/mL and 0.3 to pg/mL respectively. The extract did not promote the proliferation of HDFBs (B) or HaCaTs (C). At least 2 independent experiments with n=5 were performed for each cell type. LEC: lymphatic endothelial cell; HDFB: human dermal fibroblast; HaCaT: immortalized human keratinocyte; BEC: blood endothelial cell.

The results are summarized in FIG. 4A-4D.

Ex. 5: HPLC Profiling of the *D. gnidium* and *D. giraldii* Extracts

Figure 5A:
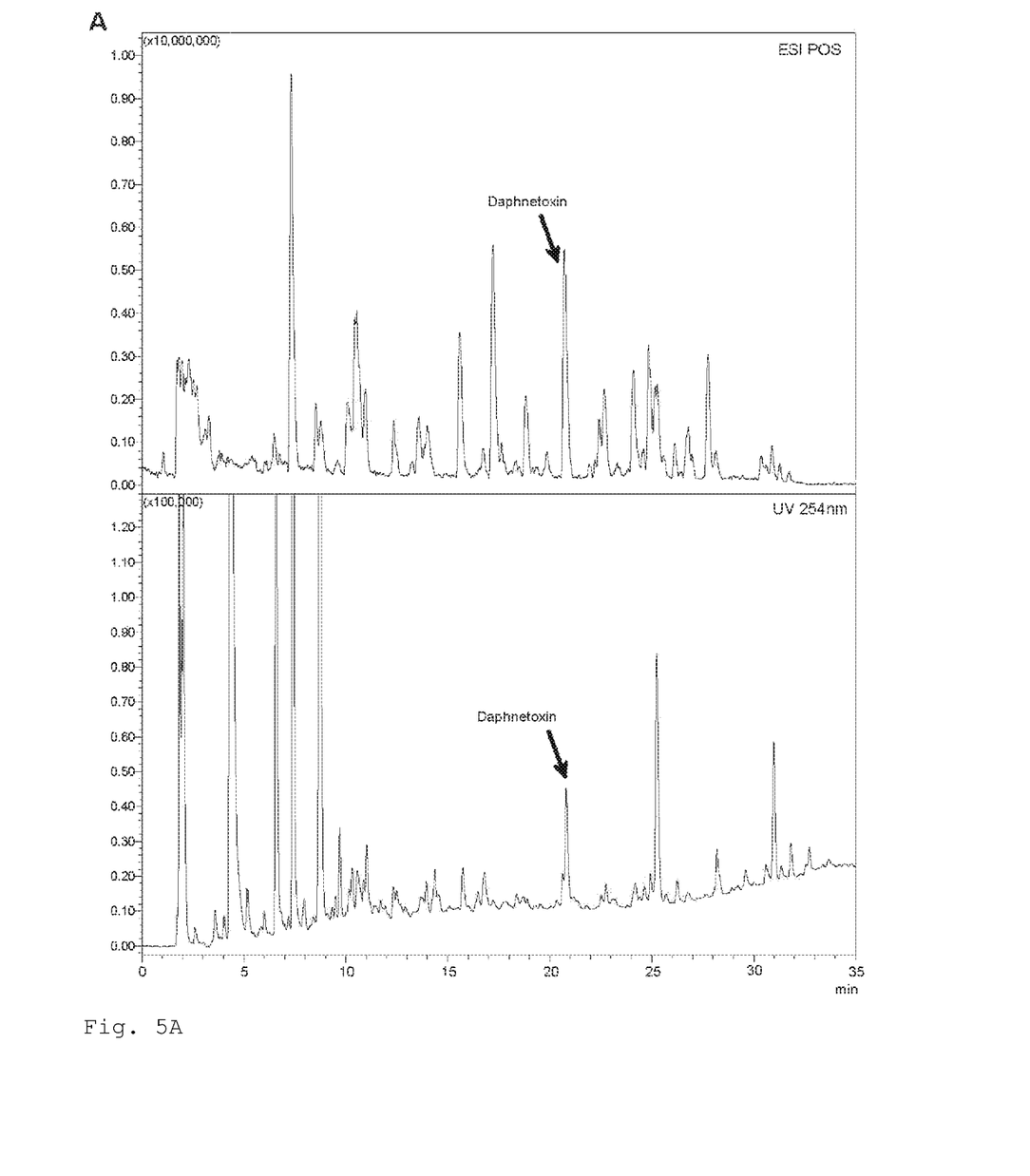
FIG. 5 shows the HPLC-UV-MS analysis of the dichloromethane extract of the leaves of *D. gnidium* (A) and *D. giraldii* (B). The arrow indicates daphnetoxin. x-axis from left to right: retention time in minutes; y-axis: milli-absorbance units.
Figure 5B:
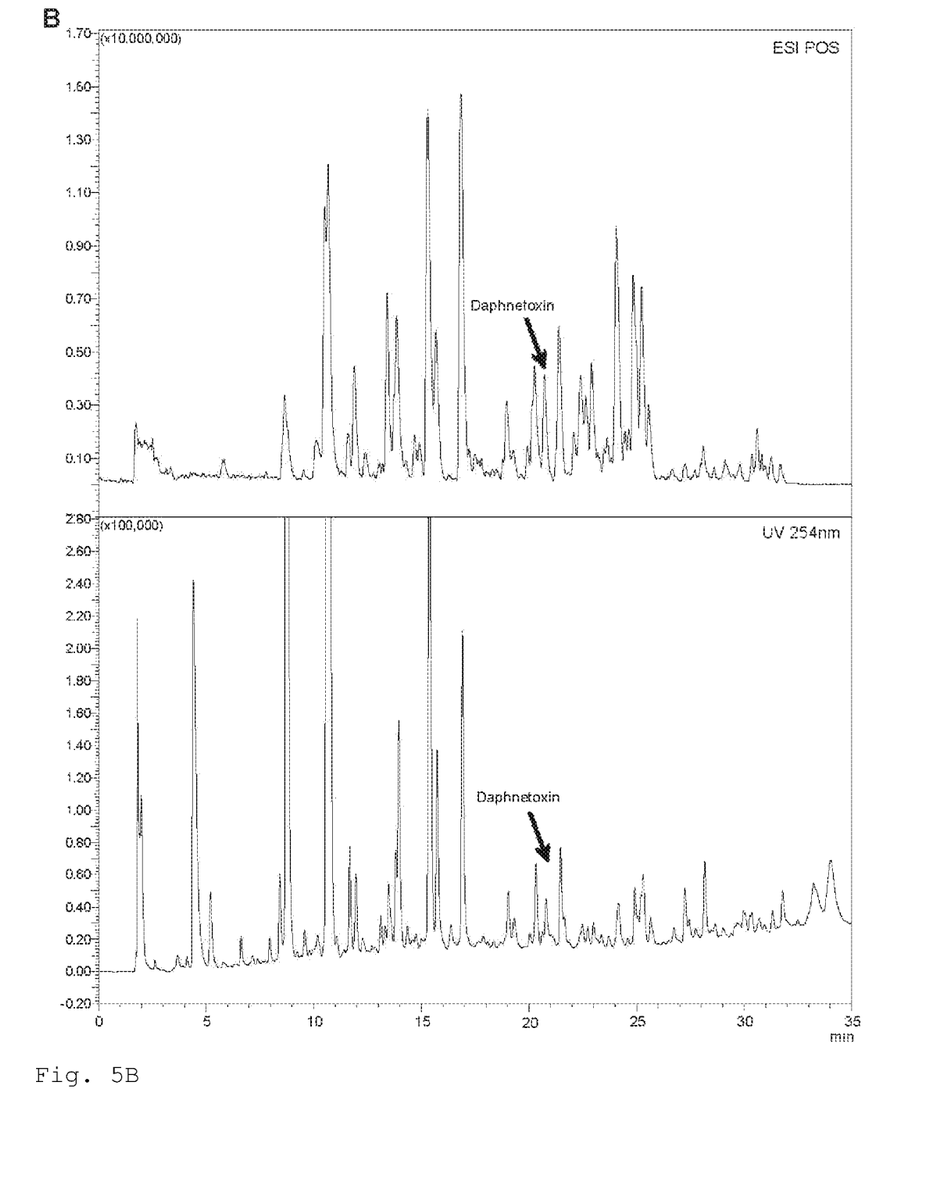

HPLC-UV-MS analysis of the dichloromethane extract of the leaves of *D. gnidium* (A) and *D. giraldii* (B). Separations were performed on a SunFire 018 column (3×150 mm id, 3 μm; Waters). The mobile phase consisted of water (A) and acetonitrile (B), both containing 0.1% HCOOH. A gradient of 5-100% B in 30 min was applied at a flow rate of 0.5 ml/min. UV 254 nm trace and base peak chromatogram (BPC) in positive ion mode are shown.

The results are summarized in FIGS. 5A and 5B.

Ex. 6: Identification of Daphnetoxin as Active Constituent

Figure 6:
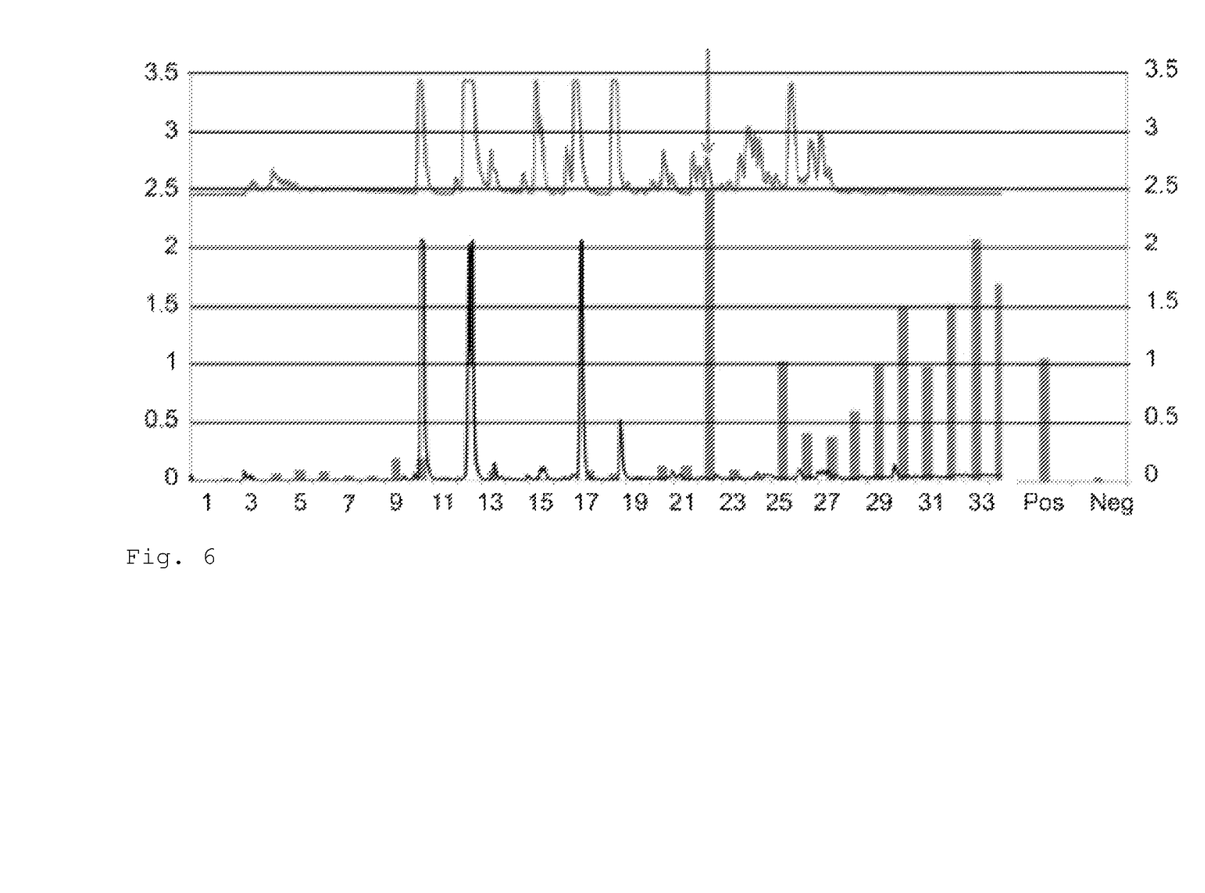
FIG. 6 shows the identification of daphnetoxin as active constituent in a fraction from *D. giraldii* dichloromethane extract by HPLC-based activity profiling. UV (black, bottom) and ESIMS (red, top) chromatographic traces. Bars: The sprouting activity of the different HPLC fractions. x-axis: retention time in minutes; y-axis: sprouts/bead. The arrow indicates daphnetoxin.

Identification of daphnetoxin as active constituent in a fraction from *D. giraldii* dichloromethane extract by HPLC-based activity profiling. Separation was performed on a SunFire $C_{18}$ column (3×150 mm id, 3 μm; Waters). The mobile phase consisted of water (A) and acetonitrile (B), both containing 0.1% HCOOH. A gradient of 5-100% B in 30 min was applied at a flow rate 0.4 ml/min. UV254 nm and ESI-MS base peak (positive ion mode) chromatograms are shown. Blue bars represent sprouting activity (number of sprouts per bead). A total of 900 μg was injected in 3 portions. 1 min fractions were collected. After evaporation to dryness, the fractions were re-dissolved in DMSO prior to testing. The data indicate that daphnetoxin presents the main active compound responsible for the activation of the LECs.

Ex. 7: LEC Sprouting of Daphnetoxin

Daphnetoxin significantly induced LEC sprouting at concentrations between 0.3 and 10 pM compared to the 0.1% DMSO control. 0.1% DMSO and 20 ng/mL of VEGF-A served as a negative and positive control respectively. Results are shown in FIG. 2B.

Figure 7:
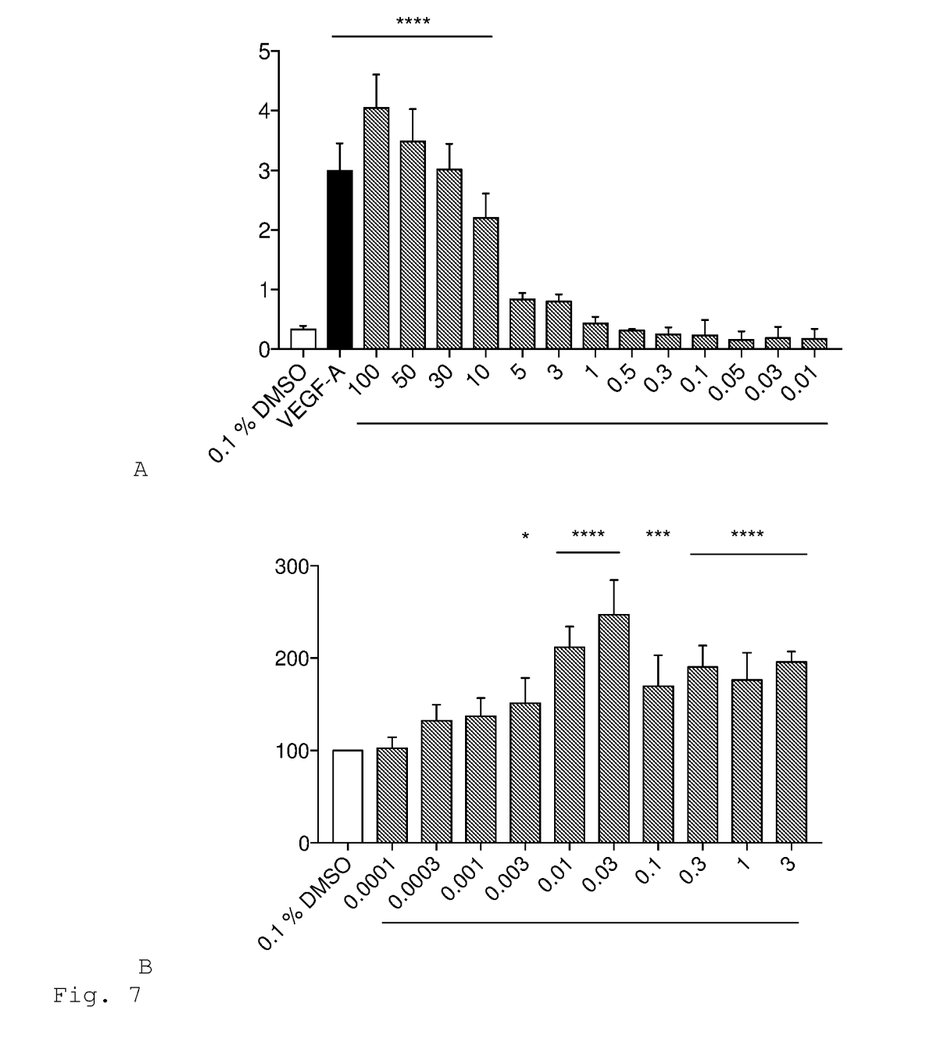

In a further experiment, effect of concentration on LEC sprouting and LEO proliferation was examined.

Daphnetoxin significantly induced LEC sprouting starting at a concentration of 10 nM. Daphnetoxin induced 4.05 sprouts/bead at 100 nM. 0.1% DMSO and 20 ng/mL of VEGF-A served as a negative and positive control respectively.

The experiment was performed once with 6 replicates and results are shown in FIG. 7A.

Daphnetoxin significantly induced LEC proliferation starting at a concentration of 0.003 pM. Daphnetoxin induced LEC proliferation most potently at 0.03 pM reaching 247±38% of control (0.1% DMSO).

The experiment was performed once with 6 replicates and results are shown in FIG. 7B.

Ex. 8: Toxicity of Extracts of *Daphne* and of Daphnetoxin

Figure 8:
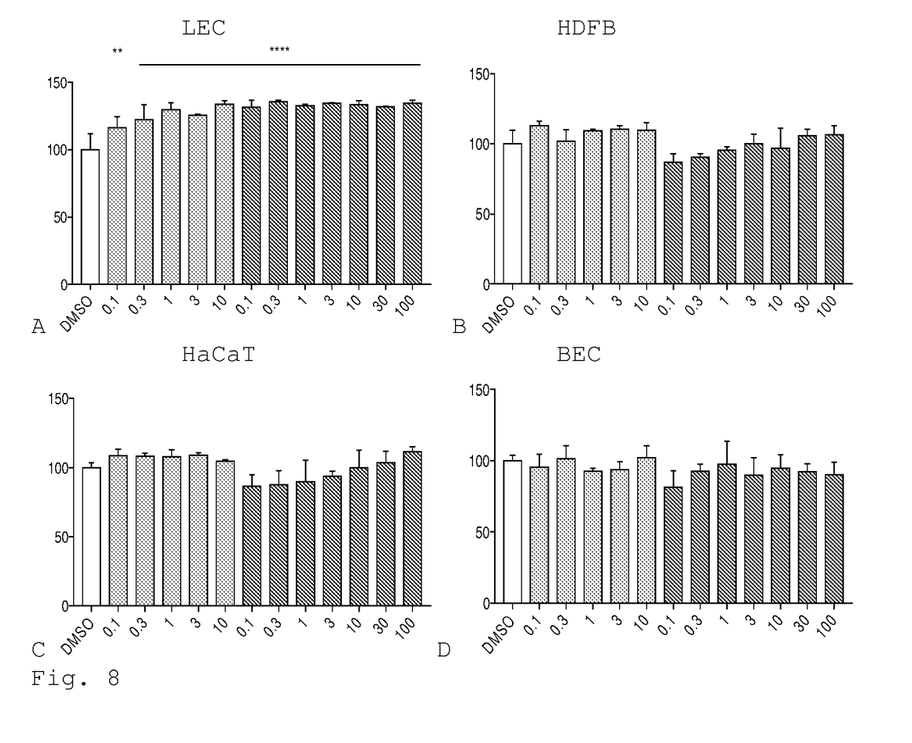
FIG. 8 shows results on toxicity as outlined in ex. 8. X-axis: white=0.1 DMSO; grey=*D. giraldi* extract (μmol/mL); black-Daphnetoxin (nanomolar). y-axis: % control.

Toxicity of the extracts according to example 2 was investigated. It was found that the *D. giraldii* extract and daphnetoxin promoted lymphatic endothelial cell proliferation specifically and did not evoke any cytotoxic effects on LEC, HDFB, HaCaT and BEC. (LEC: lymphatic endothelial cell; HDFB: human dermal fibroblast; HaCaT: immortalized human keratinocyte; BEC: blood endothelial cell). The results are summarized in FIG. 8 and indicate its usefulness in cosmetic applications.

Ex. 9: Stability Tests

The *D. giraldii* extract and daphnetoxin were subjected to stability tests. They exhibited consistent activity of LEC sprouting after prolonged exposure at 4° C., 25° C. and 50° C. for one week. It showed no differences of sprouting activity between the temperatures.

Also, HPLC-UV-MS analysis confirms stability of daphnetoxin after storage in DMSO for one week at 50° C. The results indicate that both, daphnetoxin and *D. giraldii* extracts, are sufficiently stable for use in cosmetic preparations.

The invention claimed is:

1. A cosmetic preparation for skin treatment, wherein the preparation comprises:
   plant extracts from *Daphne giraldii* and/or from *Daphne gnidium*; and
   said plant extracts contain daphnane diterpenoids in an amount of 0.00001-1 wt % based on the total weight of the cosmetic preparation.

2. The preparation of claim 1, wherein said plant extracts are present in an amount of
   0.0001-10 wt % in case of crude plant extracts, or
   0.00001-5 wt % in case of enriched extracts, or
   10 pM-10 mM in case of purified substances of said plant extracts based on the total weight of the preparation;
   are obtained by an extraction method using at least one of a solvent and a fluid selected from the group consisting of: a polar solvent, an apolar solvent, and a supercritical fluid, and/or mixtures of CO2 with C1-C3 alcohols or with acetone; and/or
   are obtained from one or more of: fresh extracts of the plant's roots, fresh extracts of the plant's green part, dried extracts of the plant's roots, or dried extracts of the plant's green part.

3. The preparation of claim 1, further comprising one or more cosmetic excipients selected from the group consisting of emollients, moisturizers, thickeners, emulsifiers, colorings, detergents, disinfectants, antioxidants, buffers, matting agents, exfoliating agents, aromas, essential oils, vitamins, UV filters, and extracellular matrix components.

4. The preparation according to claim 1 formulated as
   a liquid formulation; or
   a semisolid or solid formulation.

5. The preparation of claim 1, wherein the daphnane diterpenoids are daphnetoxin.

6. The preparation of claim 2, wherein the polar solvent is selected from the group consisting of C1-C4 alcohols, C1-C4 diols, glycerol, acetone, and ethyl acetate, in each case optionally in the presence of water.

7. The preparation of claim 2, wherein the apolar solvent is selected from the group consisting of C4-C10 alkanes, C1-C2 alkylhalogenides, and C1-C4 dialkylethers.

8. The preparation of claim 2, wherein the supercritical fluid is CO2.

9. The preparation of claim 2, wherein the polar solvent is used in the extraction method.

10. The preparation of claim 3, wherein the extracellular matrix components are selected from the group consisting of collagen, elastin, and hyaluronic acid.

11. The preparation of claim 4, wherein the liquid formulation is a gel, a lotion, a milk, an emulsion, a foam, a spray, or an oil.

12. The preparation of claim 4, wherein the semisolid or solid formulation is a cream, an ointment, a stick, or a powder.

13. A method of cosmetically treating the skin, wherein the method comprises applying to skin in need thereof a preparation according to claim 1.

14. The method of claim 13, wherein skin is treated to stimulate the lymphatic system.

15. The method of claim 13, wherein the skin is treated for
   rejuvenation of the skin,
   anti-aging of the skin,
   puffy-eye treatment,
   detoxification of the skin,
   increased firmness of the skin, and/or
   anti-swelling effect.

16. The method of claim 13, where said treatment
   increases the longevity of skin cells;
   counteracts intrinsic and/or extrinsic skin ageing;
   protects the skin; and/or
   counteracts swelling of the skin.

17. A method of stimulating the lymphatic system, the method comprising applying an effective amount of a preparation to the skin of a subject in need thereof, wherein said preparation comprises:
   plant extracts from *Daphne giraldii* and/or from *Daphne gnidium*; and
   said plant extracts contain daphnane diterpenoids, in an amount of 0.00001-1 wt % based on the total weight of the preparation.

18. The method of claim 17, wherein the daphnane diterpenoids are daphnetoxin.

* * * * *